US00PP21031P3

(12) United States Plant Patent
Dirr

(10) Patent No.: US PP21,031 P3
(45) Date of Patent: Jun. 1, 2010

(54) ***PUNICA GRANATUM* PLANT NAMED 'PIIPG-I'**

(50) Latin Name: *Punica granatum L.*
Varietal Denomination: PIIPG-I

(75) Inventor: Michael Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 12/231,648

(22) Filed: Sep. 4, 2008

(65) Prior Publication Data

US 2010/0058502 P1 Mar. 4, 2010

(51) Int. Cl.
*A01H 5/00* (2006.01)

(52) U.S. Cl. ..... Plt./210
(58) Field of Classification Search ..... Plt./210
See application file for complete search history.

(56) References Cited

OTHER PUBLICATIONS

*Punica granatum* 'PIIPG-I' Brochure hand-out at Southern Nursey Association trade show, Aug. 7-9, 2008.

*Primary Examiner*—Annette H Para
*Assistant Examiner*—Louanne C Krawczewicz Myers
(74) *Attorney, Agent, or Firm*—Greenlee Winner and Sullivan PC

(57) ABSTRACT

A new and distinct cultivar of *Punica granatum* plant named 'PIIPG-I', characterized by its compact, upright spreading growth habit, lustrous, dark green foliage, reddish-orange flowers, maroon-purple fruits, and cold hardiness to USDA Hardiness Zone 7.

4 Drawing Sheets

Genus and species of plant claimed: *Punica granatum* L.
Variety denomination: 'PIIPG-I'.

BACKGROUND OF THE INVENTION

The present invention relates to a new and distinct cultivar of *Punica granatum,* a member of the Punicaceae family, hereinafter referred to by its cultivar name 'PIIPG-I'. This cultivar is grown primarily as an ornamental for landscape use and for use as a potted plant.

The cultivar originated from open-pollination of *Punica granatum* 'Nana' (unpatented) in Watkinsville, Ga., and was selected from the progeny seedlings of this pollination by continued evaluation for fruit color and growth habit, and improved leaf and flower characteristics.

'PIIPG-I' has been asexually reproduced by softwood cuttings in Watkinsville, Ga. The characteristics of the cultivar have been stable and reproduced true-to-type in successive vegetative generations.

SUMMARY OF THE INVENTION

'PIIPG-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIPG-I' from all other varieties in commerce known to the inventor. 1) Compact, upright spreading growth habit. 2) Small, lustrous, dark green foliage. 3) Reddish-orange flowers. 4) Maroon-purple fruits. 5) Cold hardiness to USDA Hardiness Zone 7.

'PIIPG-I' is distinguished from its female parent 'Nana' by its vigor, growth habit, flower color, fruit color, and quantity of flowers and fruit produced. 'PIIPG-I' has a more vigorous, upright spreading growth habit, whereas 'Nana' has a less vigorous rounded growth habit. 'PIIPG-I' has reddish-orange flowers and maroon-purple fruits, whereas 'Nana' has orange flowers and tan to red-orange fruits. 'PIIPG-I' flowers and fruits more prolifically than 'Nana'. There are no other cultivars of *Punica granatum* with this combination of characteristics known to the inventor.

Plants of the new *Punica* can be compared to plants of the cultivar 'Eight Ball' (unpatented), which has similar colored flowers and fruits. However, in side-by-side comparisons conducted in Watkinsville, Ga., plants of the new *Punica* differed from plants of the cultivar 'Eight Ball' in the following characteristics: 1. Plants of the new *Punica* had a smaller foliage, flowers, and fruits than plants of the cultivar 'Eight Ball'; 2. Plants of the new *Punica* had a smaller and more compact growth habit reaching only about half the size of plants of the cultivar 'Eight Ball' in the same amount of time

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Punica.*

DETAILED DESCRIPTION

Figure 1:
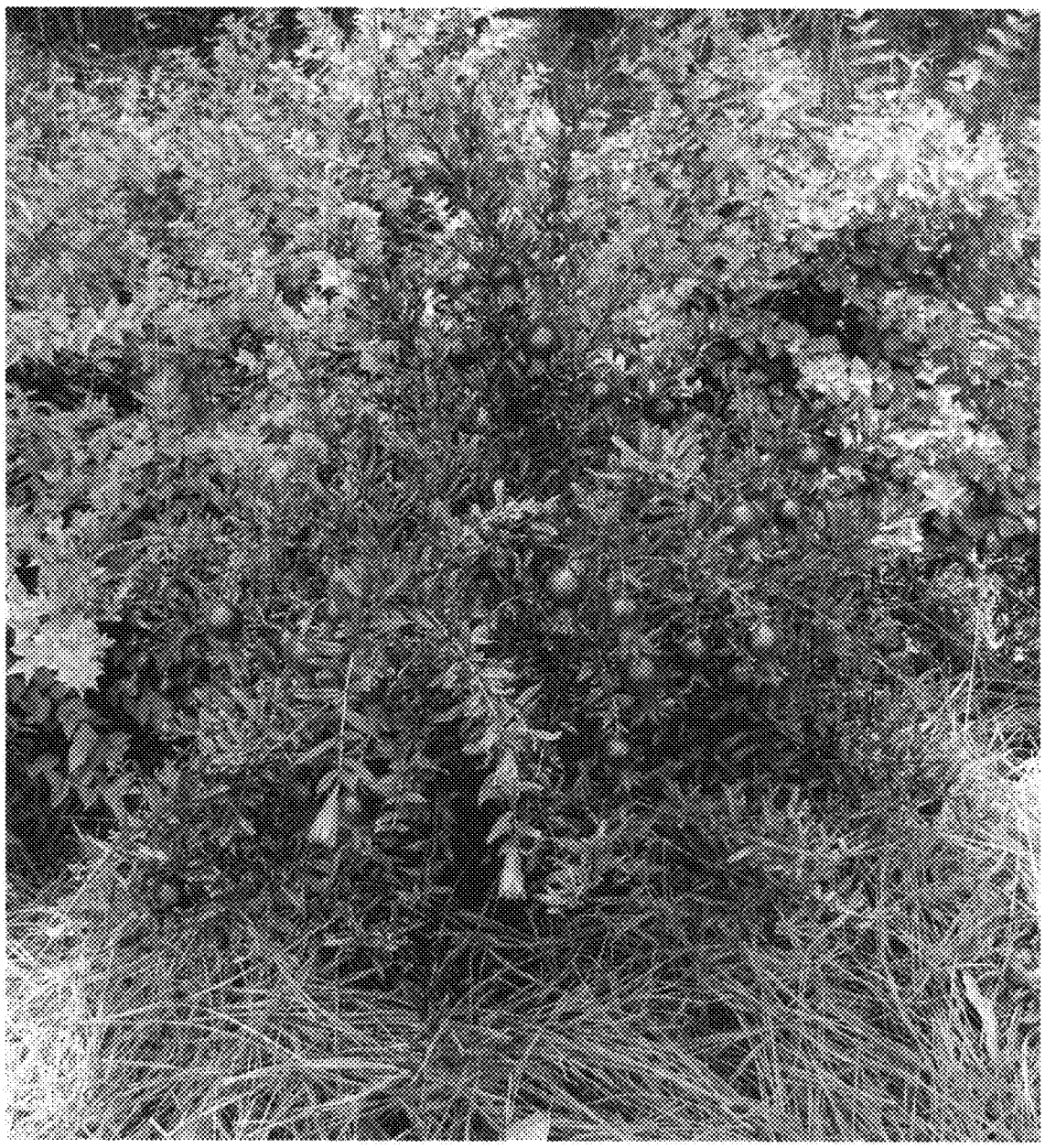
FIG. 1 shows the overall appearance of a mature plant of 'PIIPG-I'.
Figure 2:
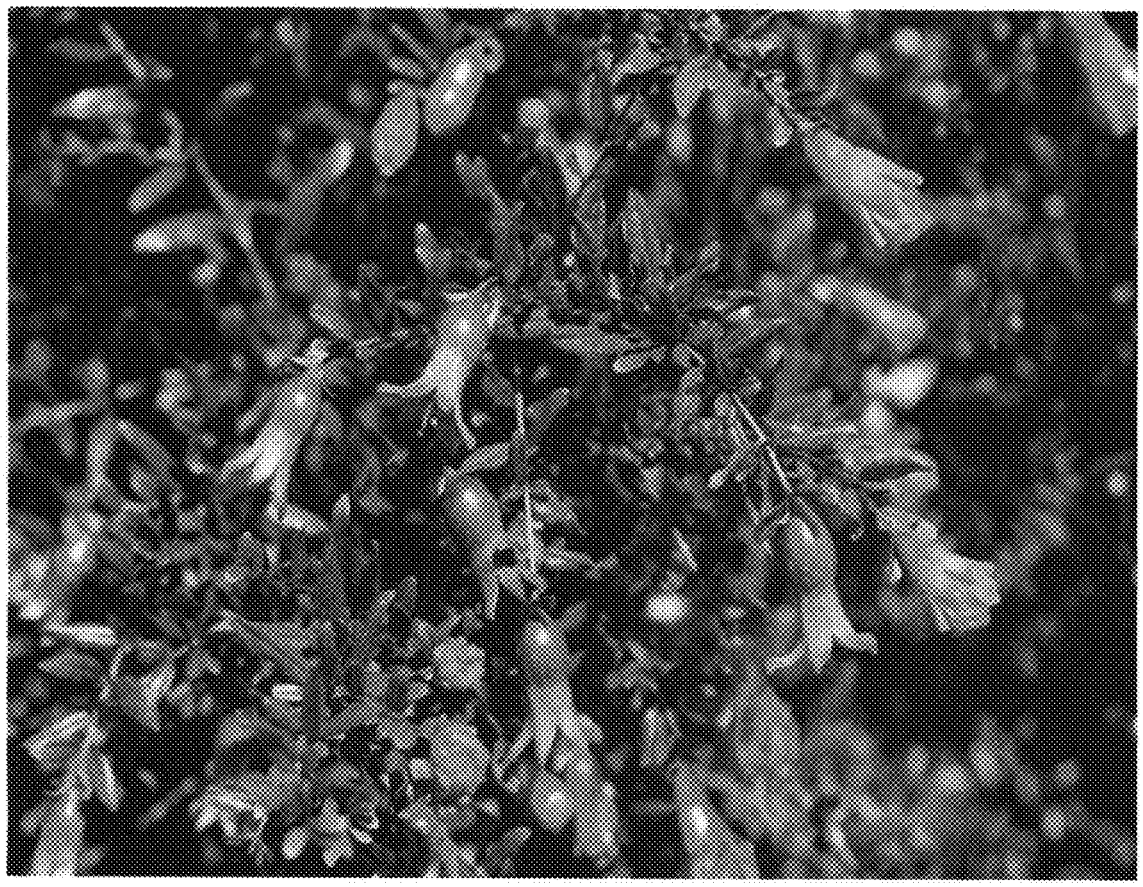
FIG. 2 shows a close-up of the flowers of 'PIIPG-I'.
Figure 3:
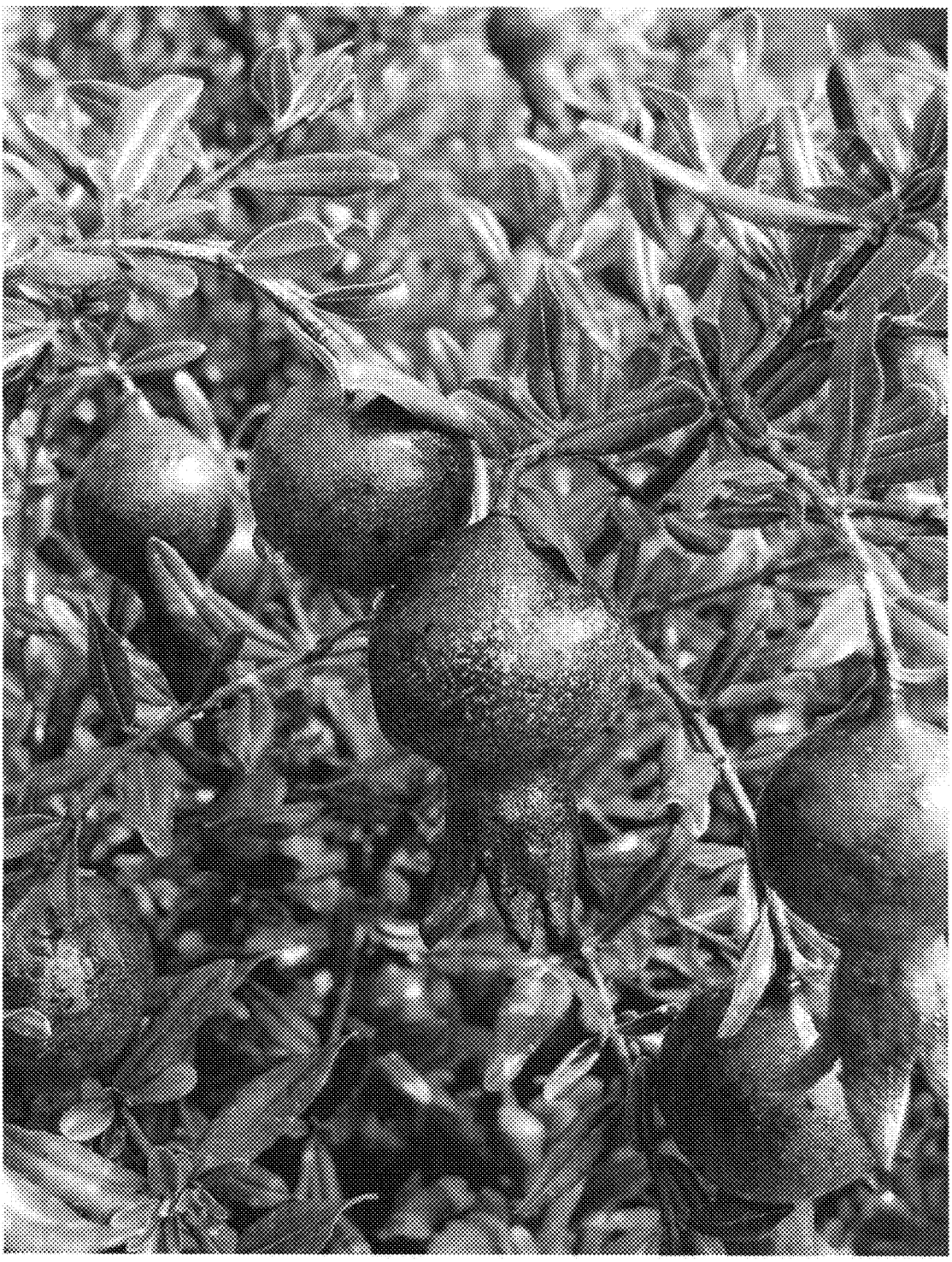
FIG. 3 shows a close-up of the fruits of 'PIIPG-I'.
Figure 4:
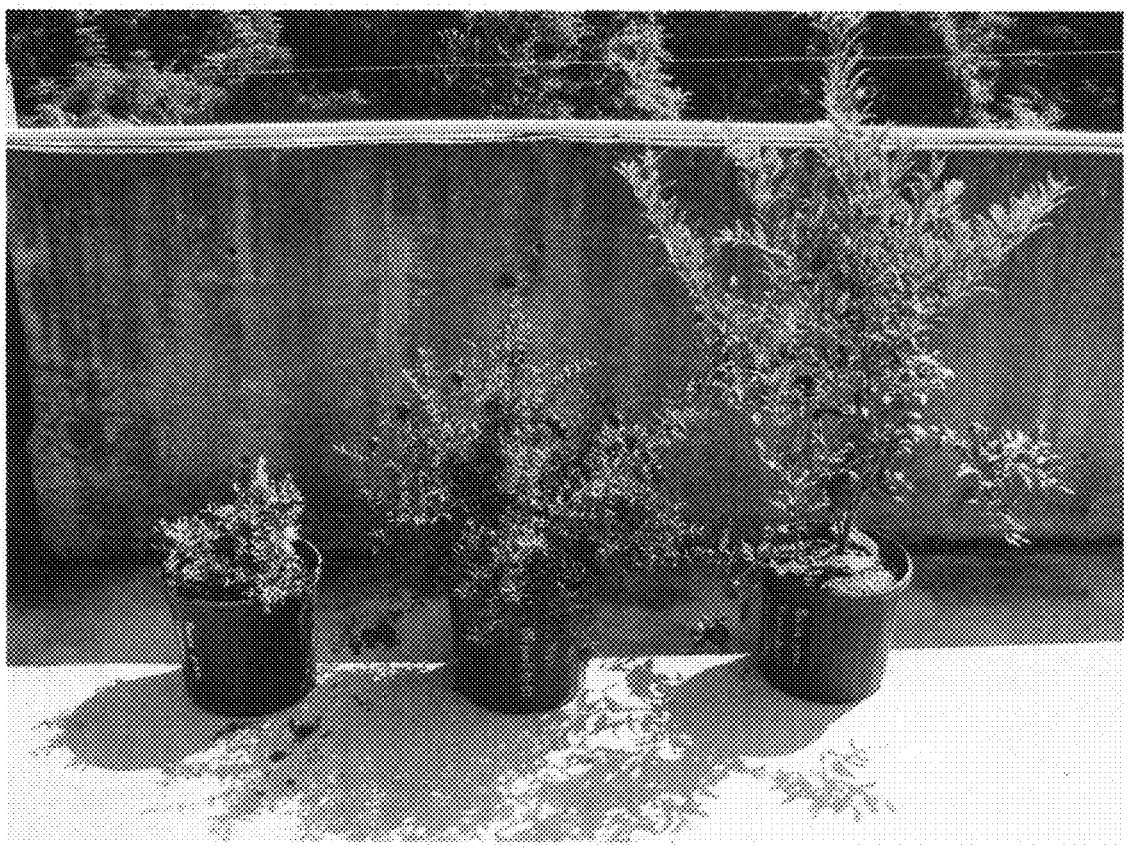
FIG. 4 shows a comparison of 'PIIPG-I' (middle) to 'Nana' (left) and 'Eight Ball' (right).

In the following description, color references are made to The Royal Horticultural Society Colour Chart, 2001 Edition, except where general terms of ordinary dictionary significance are used. Plants used for the description were grown in 11.8 L containers in full sun under outdoor conditions in a nursery in Watkinsville, Ga. Plants were 1½ years old when the description was recorded.

Botanical classification: 'PIIPG-I' is a cultivar of *Punica granatum*.

Parentage: The current variety is a progeny from an open-pollination of *Punica granatum* 'Nana'.

Propagation: Vegetatively by stem cuttings.

Plant description: The claimed variety is a freely branching, upright, spreading deciduous to semi-evergreen shrub. The plant is hardy in USDA Zones 7 to 9.

*Root description.*—Numerous, fibrous, and well-branched.

*Plant height.*—About 65 cm.

*Plant diameter.*—About 65 cm. Lateral branches having a length of about 10 to 20 cm.

*Stems.*—First year stems have a diameter of about 1.5 mm, an angled shape, and a glabrous texture.

*Pubescence.*—None.

*Exfoliation.*—On second year stems, stringy. The stem color is close to 59A, maturing close to N199B. Second year stems have a diameter of about 5 mm and color close to N199B. The main trunk is about 1.2 cm in diameter approximately 3 cm above the ground and the color is close to 199D. Approximately 1 to 10 spines are present on most lateral branches. The spines range in length from about 2 to 6 cm and are about 1 mm in width. The color of the spines is close to N199B. Lenticels are present on most stems and spines. Stems and spines have about 10 to 20 lenticels per cm of length. The round lenticels are about 1 mm in diameter and close to 199D in color.

*Internode length.*—About 6 mm.

*Vegetative buds.*—Arrangement: opposite to whorled.

*Shape.*—Ovoid.

*Size.*—About 1.5 mm in length, about 1 mm in width; Color: close to 185A.

Foliage description:

*Arrangement.*—Opposite to whorled.

*Length.*—About 1.7 cm.

*Width.*—About 5 mm.

*Shape.*—Linear-lanceolate to linear.

*Apex.*—Obtuse.

*Base.*—Cuneate.

*Margin.*—Entire.

*Texture of upper and lower leaf surfaces.*—Glabrous, lustrous.

*Venation.*—Pinnate.

*Venation color.*—Close to 137A.

*Color of emerging leaves.*—Close to 46A on the upper and lower surfaces.

*Color of mature leaves.*—On the upper surface close to 137A, and close to 146B on the lower surface.

*Fall color.*—Close to 1B.

*Petiole length.*—About 1.5 mm.

*Petiole diameter.*—About 1 mm.

*Petiole texture.*—Glabrous.

*Petiole color.*—Close to 53A on upper and lower surfaces.

Flower description:

*Flower type and habit.*—Flowers are borne singly at the terminals. Individual flowers have 5 to 7 (typically 6) petals and the calyx has 5 to 7 (typically 6) lobes. Calyx has a funnel-shaped base and flowers look similar to carnations. The calyx lobes (sepals) are about 5 mm in length and 3 mm in width, have an acute apex, a base that is fused to the calyx, lustrous texture on the upper and lower surfaces, and the color is close to 33A on the upper and lower surfaces. Individual flowers are effective for about 1 week.

*Bloom period.*—Early summer to fall.

*Fragrance.*—None.

*Flower diameter.*—About 1.5 cm.

*Flower length.*—About 3 cm.

*Flower bud diameter.*—About 8 mm.

*Flower bud length.*—About 1.5 cm.

*Flower bud shape.*—Oblong.

*Flower bud color.*—Close to 185A.

*Pedicels.*—About 2 mm in length, glabrous, and close to 53A in color.

Petals:

*Quantity.*—5 to 7 petals per flower.

*Petal length.*—1.5 cm.

*Petal width.*—8 mm.

*Petal shape.*—Spatulate with entire margin.

*Petal texture.*—Crumpled.

*Apex.*—Broad, rounded.

*Base.*—Cuneate to acute.

*Petal color.*—At peak bloom the upper and lower surfaces are close to 33A.

Stamens:

*Quantity.*—125 to 150 per flower.

*Anther diameter.*—About 1 mm.

*Anther color.*—Close to 8B.

*Filament length.*—About 1 cm.

*Filament diameter.*—About 0.5 mm in width.

*Filament color.*—Close to 8A.

*Pollen color.*—Close to 8B.

Pistils:

*Quantity/arrangement.*—One per flower, inferior.

*Pistil length.*—About 1 cm.

*Pistil diameter.*—About 1 cm.

*Pistil color.*—Close to 4C.

*Stigma quantity/shape.*—1 per pistil, roughly diamond shaped.

*Stigma color.*—Close to N144D.

*Style shape and length.*—About tubular, 5 mm.

*Style color.*—Close to 4C.

Fruit:

*Type/appearance.*—Berry, globose in shape with the persistent calyx at the apical end.

*Fruit length.*—About 3.5 cm.

*Fruit diameter.*—About 2.5 cm. Fruit stem length is about 2 mm and caliper is about 1 mm and color is close to N186A.

*Fruit color at maturity.*—The main body color is close to 187A, and the fruit has blotches close to N186C. The surface or skin of the fruit is lustrous, leathery, and has round lenticels about 1 mm in diameter and close to 199D in color. The fruit, which are typically left on the plant for ornamental appeal, have a tendency to crack late in the season (mid to late fall).

*Quantity.*—The number of fruit per plant varies widely depending on the size and maturity of the plant. This cultivar is primarily grown as an ornamental and is not intended to be edible. Since this is a dwarf cultivar, the fruit remain small and bitter.

*Seeds.*—About 5 mm in length, about 3 mm in width, close to 199D, and each berry contains 50 to 100 seeds.

Disease/pest resistance: No specific pest or disease resistance/susceptibility has been observed.

I claim:

1. A new and distinct *Punica granatum* plant named 'PIIPG-I', substantially as illustrated and described herein.

* * * * *